United States Patent [19]

Zaffaroni et al.

[11] 4,317,884

[45] Mar. 2, 1982

[54] METHOD FOR THE PRODUCTION OF YEAST ON ETHANOL AND MEANS THEREFOR

[75] Inventors: Pasquale Zaffaroni, Mentana; Antonio Senni, Rome; Lamberto Formiconi, Monterotondo, all of Italy

[73] Assignee: Snamprogetti S.p.A., Milan, Italy

[21] Appl. No.: 941,399

[22] Filed: Sep. 11, 1978

[30] Foreign Application Priority Data

Oct. 5, 1977 [IT] Italy .............................. 28277 A/77

[51] Int. Cl.³ .................... C12N 1/32; C12N 1/16; C12R 1/645; C12R 1/72
[52] U.S. Cl. .............................. 435/247; 435/255; 435/804; 435/813; 435/911; 435/921; 435/938; 426/656
[58] Field of Search .............. 435/247, 255, 804, 813, 435/938, 921, 911; 426/656

[56] References Cited

U.S. PATENT DOCUMENTS 3,243,354  3/1966  Nakao et al. .................. 435/911
3,982,998  9/1976  Hitzman et al. ............... 435/247
4,168,201  9/1979  Wegner ......................... 435/247
4,229,543 10/1980  Tonomura et al. ............. 435/247

OTHER PUBLICATIONS

Lodder, *The Yeasts*, North-Holland Publishing Co., Amsterdam, (1970), pp. 1066-1068.

*Primary Examiner*—Thomas Wiseman
*Attorney, Agent, or Firm*—Morgan, Finnegan, Pine, Foley & Lee

[57] ABSTRACT

For the production of biological masses of microbial origin, the yeast strain NRRL-Y 11119 uses ethanol as a carbon source and an energy source simultaneously. Proteic biomasses of a very good quality are obtained.

6 Claims, No Drawings

METHOD FOR THE PRODUCTION OF YEAST ON ETHANOL AND MEANS THEREFOR

This invention relates to the production of a microbial mass by culturing a yeast which is capable of using ethanol as the single carbon source and energy source with a high efficiency and at a high temperature.

Due to the speed of multiplication of the microorganisms and their high protein contents, the production of microbial biomasses is a very quick method for producing proteins.

For the production of biomasses there have been exploited in the past scraps of carbohydrate materials such as sugar molasses or paper-mill sulfite liquors.

In more recent times, on the basis of the considerable availability and low price of petroleum, methods of production of biomasses have been perfected which used as the substrate both crude petroleum fractions and mixtures of highly purified nor. paraffins.

The use of such petroleum substrates shows some difficulties of technological nature, due to their insolubility in water, the great amounts of oxygen which are required for their assimilation by the micro-organisms and the large heat build up during fermentation.

In addition, the production cost of the biomasses is made higher due to the necessity of thoroughly purifying the substrate and/or carefully washing the as produced biomass in order to remove the potentially hazardous petroleum residues therefrom.

These difficulties are removed if the production of biomasses is carried out by using as the substrates the lower alcohols such as methanol and ethanol.

As a matter of fact, their complete solubility in water, their volatility and the fact of their being available at a high degree of purity make it possible to obtain a biomass which is free from undesirable residues. Their miscibility with water prevents mixture problems such as those which are experienced with the petroleum fractions, whereas the fact of their containing oxygen in their very molecule decreases the quantity of oxygen required by them for assimilation: the result is the advantage that the production of biomasses is accompanied by a reduced heat build up so that also the costs for cooling are concurrently reduced.

Ethanol is used by a great number of micro-organisms and would be the ideal substrate for the production of biomasses, but it has a rather high cost.

The use of ethanol for the production of biomasses may become competitive if the advantages it affords are such as to offset the shortcoming of its higher cost as compared with that of the other substrates.

It is to be noted, at the outset, that ethanol is a component of the human diet so that there is no problem due to the possible presence of residues of ethanol in the biomass.

The yeast strain used by us (SP 1296) has been isolated from a preparation which has been used as an essential ingredient in the production of a traditional food, of which it was not an occasional pollutant, so that any toxicity or pathogenic character of the strain can be excluded even in the event of a direct human use.

The strain SP 1296 has been identified taxonomically as *Candida valida,* according to the classification suggested by the book: J. Lodder ed. The Yeast: A taxonomic study (1970).

At page 106 of the book, there can be read: "*C. valida* has the same morphological and physiological properties as *Pichia membranaefaciens* and may be regarded as its imperfect form".

The source from which the strains described therein of *C. valida* (page 1068) and *P. membranaefaciens* (pages 505–506) have been isolated indicate that these two species are widespread in foods and beverages of common use, thus giving a further confirmation to the hypothesis that our strain ought not to give rise to problems of toxicity even in the case of a direct consumption by humans.

To these advantages of toxicological significance, our strain adds considerable advantages of a technological nature: as a matter of fact, it is characterized by a high multiplication speed (duplication time 1 hour 6 mins.), a fair tolerance for ethanol, a high growth temperature (up to 40° C.), and above all, a very high yield referred to ethanol (up to 80%) and all these factors considerably contribute towards a high productivity and thus the economical advantage of the instant method of producing yeast from ethanol as compared with other commercial biomass production methods.

The strain in question has been deposited with the collection of cultures of ARS (Agricultural Research Service, USA Dept. of Agriculture, Peoria, Ill.) where it has been allotted the number NRRL-Y 11119.

The strain can be cultured both in discontinuous or continuous cultures but its properties are better exploited in a continuous culture.

In practice, the method comprises inoculating with the strain SP 1296 a culturing medium containing the essential elements (N, P, K, Mg, Fe, Ca, Zn), the growth factors (yeast extract and biotin), mineral trace elements and ethanol as the source of carbon and energy. The broth is incubated at a temperature comprised between 30° C. and 41° C., preferably between 37° C. and 40° C., the pH being maintained between 2.5 and 6.5, preferably between 4 and 5, a continuous oxygen supply, such as in the form of air, being provided.

The yeast cells which are multiplied at the expenses of the nutrients which have been supplied, are collected by sedimentation or filtration washed with water and heat dried.

The as obtained biomass can be used as such as a proteinic addition to foods and fodders, or noble products can be extracted therefrom such as proteins, aminoacids, nucleic acids and others to be used in food formulations.

The invention is illustrated but not limited by the ensuing Examples.

EXAMPLE 1

Two 20-liter jars containing 12 liters of the following culturing medium:

| | |
|---|---|
| $KH_2PO_4$ | 1.5 grams per liter |
| $NaH_2PO_4 \cdot H_2O$ | 0.5 |
| $(NH_4)_2SO_4$ | 5.0 |
| $NH_4Cl$ | 5.0 |
| $MgSO_4 \cdot 7H_2O$ | 0.5 |
| $FeSO_4 \cdot 7H_2O$ | 4.0 milligrams per liter |
| $ZnSO_4 \cdot 7H_2O$ | 4.0 |
| $CaCl_2$ | 4.0 |
| Yeast extract | 0.5 grams per liter |
| Trace element soln. | 2.0 mls per liter, | are employed for the test.

The solution of trace elements had the following composition:

| | |
|---|---|
| $H_3BO_3$ | 500 milligrams |
| $CuSO_4 \cdot 5H_2O$ | 200 milligrams |
| KI | 10 |
| $MnSO_4 \cdot 7H_2O$ | 500 |
| $CoCl_2 \cdot 6H_2O$ | 10 |
| $MoO_3$ | 10 |
| $H_2O$ at pH 2 (by HCl) | 1 liter |

The medium-containing jars, the medium having a pH of 5.5, were sterilized at 116° C. for 30 mins. and inoculated with the 5% volume/volume of a previously prepared culture of the strain SP 1296 which contained 29 g/liter of biomass. To the jars were added, respectively, 2% and 4% volume/volume of ethanol and were incubated at 39° C., 800 rpm, the aeration being progressively increased from 0.30 to 0.75 volume/volume per minute. The pH was controlled at 4.5 with KOH.

The biomass which was produced when the ethanol which was present had all been used up, is tabulated below together with other data:

| Initial ethanol | Incubation time hrs. | Final biomass g/liter | Yield g/100 g |
|---|---|---|---|
| 2% vol/vol = 16 g/liter | 10 | 12.40 | 77.5 |
| 4% vol/vol = 32 g/liter | 16 | 16.56 | 51.8 |

EXAMPLE 2

To a fermenter having an effective capacity of 6.5 liters and containing a well developed culture of the strain SP 1296 in the following culturing medium:

| | |
|---|---|
| $KH_2PO_4$ | 1.5 grams/liter |
| $NaH_2PO_4 \cdot H_2O$ | 0.5 |
| $(NH_4)_2SO_4$ | 10.0 |
| $NH_4Cl$ | 10.0 |
| $MgSO_4 \cdot 7H_2O$ | 0.5 |
| $FeSO_4 \cdot 7H_2O$ | 10.0 milligrams/liter |
| $CaCl_2$ | 10.0 milligrams/liter |
| $ZnSO_4 \cdot 7H_2O$ | 10.0 |
| Solution of traxe elements (EX. 1) | 5.0 milliliters/liter |
| Yeast extract | 0.5 grams/liter |
| Ethanol | 40 grams/liter | was continuously added sterile culturing medium (pH 5.0 sterilized at 116° C. during 30 mins., without ethanol, which was sterilized separately by filtration) and simultaneously an identical volume of broth culture was drawn, The fermenter was kept at a temperature of 39° C.: it was equipped with four wave-breakers and 2 turbine rotors which were rotated at 2,800 rpm. The pH of the broth culture was maintained at 5.0 by automatic addition of KOH. Instead of KOH, ammonia can be used for controlling the pH but the elimination of a fair fraction of ammonium salts in the formulation of the culturing medium can be eliminated.

Foam was controlled by the addition of a foam-killer such as polypropyleneglycol.

As the dilution velocity, D, that is the ratio of the flow of the incoming sterile medium (identical to that of the exiting broth culture) to the static volume of the culture had reached 0.34, the concentration of the biomass in the exiting broth culture was 32.3 grams/liter whereas the concentration of the ethanol (residual) was 20 milligrams per liter. The yield of the conversion of the ethanol to biomass was then 80.8% and the hourly output was 10.98 g/liter. The biomass, washed and dried, had the following composition:

| | |
|---|---|
| Ash | 5.90% |
| Total carbohydrates | 25.67% |
| Crude fibre | 3.18% |
| RNA | 5.50% |
| DNA | 1.00% |
| Raw proteins (Kjedahl) $N \times 6.25$) | 52.29% |
| Proteins (biuret) | 49.60% |
| Total lipids | 6.78% |
| Fatty acids | 5.50% |

The percentage distribution of the fatty acids was as follows:

| | |
|---|---|
| $C_{14}$ | 2.81% |
| $C_{15}$ | 0.90% |
| $C_{16}$ | 14.45% |
| $C_{16:1}$ | 5.15% |
| $C_{17}$ | 1.14% |
| $C_{18}$ | 2.97% |
| $C_{18:1}$ | 23.15% |
| $C_{18:2}$ | 21.26% |
| $C_{18:3}$ | 23.61% |
| Others | 4.56% |

The contents of aminoacids of the dry biomass (grams per 100 grams of dry matter) was the following:

| | |
|---|---|
| Lysine | 2.84 |
| Istidine | 0.83 |
| Arginine | 1.87 |
| Aspartic acid | 2.90 |
| Threonine | 1.72 |
| Serine | 1.16 |
| Glutamic acid | 5.09 |
| Proline | 1.08 |
| Glicine | 1.31 |
| Alanine | 1.75 |
| Cysteine | not determined |
| Valine | 2.85 |
| Methionine | 0.76 |
| Isoleucine | 1.59 |
| Leucine | 2.63 |
| Tirosine | 1.38 |
| Phenylalanine | 1.57 |
| Triptophane | not determined |

We claim:

1. A method for the production of a microbial biomass, said method comprising innoculating a culture medium which contains ethanol as the source of carbon and energy with the yeast strain NRRL-Y 11119 and aerobically incubating said culture medium.

2. A method as defined in claim 1 wherein the culturing medium is incubated at a temperature between 30° and 41° C.

3. A method as defined in claim 1 wherein the culturing medium is incubated at a temperature between 37° and 41° C.

4. A method as defined in claim 2 wherein the pH is maintained between 2.5 and 6.5

5. A method as defined in claim 3 wherein the pH is maintained between 4 and 5.

6. A method as defined in claim 1 wherein the biomass is separated from the culturing medium by sedimentation or filtration.

* * * * *